United States Patent
Lee et al.

(10) Patent No.: US 9,058,682 B2
(45) Date of Patent: Jun. 16, 2015

(54) APPARATUS AND METHOD FOR VIRTUAL VIEW GENERATION ON MULTI-VIEW IMAGE RECONSTRUCTION SYSTEM BY VIRTUAL EMISSION OF X-RAYS

(71) Applicant: SAMSUNG ELECTRONICS CO., LTD., Suwon-si (KR)

(72) Inventors: Jae Hak Lee, Yongin-si (KR); Jong Ha Lee, Hwaseong-si (KR); Young Hun Sung, Hwaseong-si (KR); Kang Eui Lee, Seoul (KR); Kwang Eun Jang, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 266 days.

(21) Appl. No.: 13/728,338

(22) Filed: Dec. 27, 2012

(65) Prior Publication Data

US 2013/0177213 A1 Jul. 11, 2013

(30) Foreign Application Priority Data

Jan. 10, 2012 (KR) .................. 10-2012-0002813

(51) Int. Cl.
| | |
|---|---|
| G06K 9/00 | (2006.01) |
| G06T 17/00 | (2006.01) |
| G06T 11/00 | (2006.01) |
| A61B 6/02 | (2006.01) |
| A61B 6/03 | (2006.01) |
| A61B 6/00 | (2006.01) |

(52) U.S. Cl.
CPC .............. *G06T 17/00* (2013.01); *A61B 6/025* (2013.01); *A61B 6/03* (2013.01); *A61B 6/5223* (2013.01); *G06T 11/008* (2013.01); *G06T 2211/412* (2013.01); *G06T 2211/436* (2013.01)

(58) Field of Classification Search
None
See application file for complete search history.

(56) References Cited

U.S. PATENT DOCUMENTS

| | | | |
|---|---|---|---|
| 5,420,788 A | 5/1995 | Vissers | |
| 6,522,712 B1 | 2/2003 | Yavuz et al. | |
| 7,529,398 B2 * | 5/2009 | Zwirn et al. | 382/131 |
| 7,773,721 B2 * | 8/2010 | Wu et al. | 378/21 |
| 8,594,407 B2 * | 11/2013 | Jerebko et al. | 382/131 |
| 2008/0228062 A1 * | 9/2008 | Zwirn et al. | 600/407 |
| 2011/0044546 A1 * | 2/2011 | Pan et al. | 382/195 |

(Continued)

FOREIGN PATENT DOCUMENTS

| | | |
|---|---|---|
| KR | 10-0801968 B1 | 2/2008 |
| KR | 10-2010-0125292 A | 11/2010 |

(Continued)

*Primary Examiner* — Tahmina Ansari
(74) *Attorney, Agent, or Firm* — Sughrue Mion, PLLC (57) ABSTRACT

Provided is an apparatus and method for generating a virtual view in an image reconstruction system which uses multiple views. In the image reconstruction system which uses multiple views, the virtual view generating apparatus may receive original view projection images that are generated by emitting X rays toward an object via original views, three-dimensionally reconstruct the object by using the original view projection images, generate original view reprojection images by virtually emitting X-rays toward the reconstructed 3D object via the original views, estimate a motion of the reconstructed 3D object with respect to at least two of the original view reprojection images using a block-based motion estimation scheme, and generate an intermediate view projection image with respect to the at least two of the original view reprojection images by using information relating to the estimated motion.

24 Claims, 9 Drawing Sheets

(56) References Cited

U.S. PATENT DOCUMENTS

2011/0069237 A1 3/2011 Wang et al.
2011/0135054 A1* 6/2011 Gregerson et al. .............. 378/19
2013/0177213 A1* 7/2013 Lee et al. ...................... 382/107

FOREIGN PATENT DOCUMENTS

| KR | 10-2011-0020969 A | 3/2011 |
| KR | 10-2011-0056837 A | 5/2011 |

* cited by examiner

APPARATUS AND METHOD FOR VIRTUAL VIEW GENERATION ON MULTI-VIEW IMAGE RECONSTRUCTION SYSTEM BY VIRTUAL EMISSION OF X-RAYS

CROSS-REFERENCE TO RELATED APPLICATION(S)

This application claims priority under 35 U.S.C. §119(a) from Korean Patent Application No. 10-2012-0002813, filed on Jan. 10, 2012, in the Korean Intellectual Property Office, the entire disclosure of which is incorporated herein by reference for all purposes.

BACKGROUND

1. Field

The following description relates to a method and an apparatus for virtually generating a predetermined view between sparse view intervals obtained by using a tomosynthesis system.

2. Description of Related Art

As an example of a general tomosynthesis system, in an aspect of reconstructing a three-dimensional (3D) volume from a total of 21 view projection images that are obtained based on a scan range from −30 degrees to +30 degrees and a view interval of 3 degrees, two problems may be found. First, due to sparse view intervals, a resolution of the reconstructed 3D volume may be poor. Second, in a stereoscopic virtualization aspect of the reconstructed 3D volume, due to reprojection, a serious blur may occur with respect to a view, for example, 1.5 degrees, except for the obtained view intervals. In addition, it may be impossible to consistently produce high quality views. Therefore, there is a desire to virtually generate a predetermined view between sparse view intervals from a reconstructed 3D volume. When increasing or visualizing a volume resolution by applying the virtually generated view for reconstruction, it is possible to consistently produce a high quality image.

To generate a virtual view, matching between neighboring sparse views is required as key technology. An intermediate view may be generated by obtaining motion information with respect to all of pixels included in neighboring projection images through matching and by employing the motion information. An inter-view simple or straight average method or a view generation method using a directional interpolation that is applied in a conventional art to generate a view may be applicable to a dense view interval, for example, 0.2 to 0.4 degrees, such as an interval typically used in conjunction with computed tomography (CT), and may not be applicable to a sparse view interval, for example, 2 to 5 degrees, such as an interval typically used in conjunction with a tomosynthesis system.

SUMMARY

In one general aspect, there is provided an apparatus for generating a virtual view in an image reconstruction system, the apparatus including a receiver which receives original view projection images that are generated by emitting X rays toward an object via original views, a three-dimensional (3D) reconstruction generator which generates a 3D object by three-dimensionally reconstructing the object by using the original view projection images, a reprojection image generator which generates original view reprojection images by virtually emitting X-rays toward the reconstructed 3D object via the original views, a motion estimator which estimates a motion of the reconstructed 3D object with respect to at least two of the original view reprojection images by using a motion estimation scheme, and an intermediate view generator which generates an intermediate view projection image with respect to the at least two of the original view reprojection images by using information relating to the at least two of the original view reprojection images that is estimated by the motion estimator.

The original view projection images may include data that is generated based on a partial isometric system.

The motion estimator may use a linear motion estimation algorithm for estimating the motion of the reconstructed 3D object with respect to the at least two of the original view reprojection images, and may estimate a motion with respect to the intermediate view projection image that is generated by the intermediate view generator.

When estimating the motion with respect to the intermediate view projection image, the motion estimator may estimate the motion with respect to the intermediate view projection image by assigning a first contribution value to a first one of the at least two of the original view reprojection images and a second contribution value to a second one of the at least two of the original view reprojection images, wherein when a determination that the first one of the at least two of the original view reprojection images is closer to the intermediate view projection image is made based on the intermediate view projection image, the first contribution value is greater than the second contribution value, and when a determination that the second one of the at least two of the original view reprojection images is closer to the intermediate view projection image is made based on the intermediate view projection image, the second contribution value is greater than the first contribution value.

The reprojection image generator may generate intermediate view reprojection images by virtually emitting X rays toward the reconstructed 3D object via intermediate views. The motion estimator may estimate a motion of the reconstructed 3D object with respect to two adjacent reprojection images from among the original view reprojection images and the generated intermediate view reprojection images by using the two adjacent reprojection images.

The reprojection image generator may generate intermediate view reprojection images by virtually emitting X rays toward the reconstructed 3D object via intermediate views. The intermediate view generator may generate a motion reliability map which corresponds to a first intermediate view that is classified as a reliable area and a second intermediate view that is classified as an unreliable area by using motion information estimated by the motion estimator, and may generate the intermediate view projection image by using the generated original view reprojection images in conjunction with a motion interpolation scheme to fill the reliable area and by using at least one of the generated intermediate view reprojection images to fill the unreliable area.

The motion estimator may estimate a motion with respect to the at least two of the original view reprojection images based on a forward motion estimation and a backward motion estimation, and the intermediate view generator may generate the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

The reprojection image generator may generate intermediate view reprojection images by virtually emitting X rays toward the reconstructed 3D object via intermediate views. The intermediate view generator may generate a motion reliability map which corresponds to a first intermediate view that is classified as a reliable area and a second intermediate view which is classified as an unreliable area by using motion information estimated by the motion estimator, and may generate the intermediate view projection image by using the generated intermediate view reprojection images to fill the unreliable area, and using a weighted averaging of an image that is generated by interpolating the at least two of the original view reprojection images and at least one of the intermediate view reprojection images to fill the reliable area.

When using the weighted averaging to fill the reliable area of the motion reliability map, the intermediate view generator may increase a first weight which is assigned to the at least one of the intermediate view reprojection images and may decrease a second weight which is assigned to the image that is generated by interpolating the at least two of the original view reprojection images when a determination is made that a distance between the intermediate view reprojection image and the original view reprojection image has decreased.

The motion estimator may estimate a motion with respect to the at least two of the original view reprojection images based on a forward motion estimation and a backward motion estimation, and the intermediate view generator may generate the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

In another general aspect, there is provided a method for generating a virtual view in an image reconstruction system, the method including receiving original view projection images that are generated by emitting X rays toward an object via original views, generating a 3D object by three-dimensionally reconstructing the object by using the original view projection images, generating original view reprojection images by virtually emitting X-rays toward the reconstructed 3D object via the original views, estimating a motion of the reconstructed 3D object with respect to at least two of the original view reprojection images by using a motion estimation scheme, and generating an intermediate view projection image with respect to the at least two of the original view reprojection images by using motion information.

The original view projection images may include data that is generated based on a partial isometric system.

The estimating may include using a linear motion estimation algorithm for estimating the motion of the reconstructed 3D object with respect to the at least two of the original view reprojection images, and estimating a motion with respect to the generated intermediate view projection image.

When estimating the motion with respect to the generated intermediate view projection image, the estimating may include estimating the motion with respect to the intermediate view projection image by assigning a first contribution value to a first one of the at least two of the original view reprojection images and a second contribution value to a second one of the at least two of the original view reprojection images, wherein when a determination that the first one of the at least two of the original reprojection images is closer to the intermediate view projection image is made based on the intermediate view projection image, the first contribution value is greater than the second contribution value, and when a determination that the second one of the at least two of the original view reprojection images is closer to the intermediate view projection image is made based on the intermediate view projection image, the second contribution value is greater than the first contribution value.

The method may further include generating intermediate view reprojection images by virtually emitting X rays toward the reconstructed 3D object via intermediate views. The estimating may include estimating a motion of the reconstructed 3D object with respect to two adjacent reprojection images from among the original view reprojection images and the generated intermediate view reprojection images by using the two adjacent reprojection images.

The method may further include generating intermediate view reprojection images by virtually emitting X rays toward the reconstructed 3D object via intermediate views. The generating of the intermediate view projection image may include generating a motion reliability map which corresponds to a first intermediate view that is classified as a reliable area and a second intermediate view that is classified as an unreliable area by using estimated motion information, and generating the intermediate view projection image by using the generated original view reprojection images in conjunction with a motion interpolation scheme to fill the reliable area and by using at least one of the generated intermediate view reprojection images to fill the unreliable area.

The generating of the intermediate view projection image may include estimating a motion with respect to the at least two of the original view reprojection images based on a forward motion estimation and a backward motion estimation and generating the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

The method may further include generating intermediate view reprojection images by virtually emitting X rays toward the reconstructed 3D object via intermediate views. The generating of the intermediate view projection image may include generating a motion reliability map which corresponds to a first intermediate view that is classified as a reliable area and a second intermediate view that is classified as an unreliable area and by using estimated motion information, and generating the intermediate view projection image by using the generated intermediate view reprojection images to fill the unreliable area, and using a weighted averaging of an image that is generated by interpolating the at least two of the original view reprojection images and at least one of the intermediate view reprojection images to fill the reliable area.

When using the weighted averaging to fill the reliable area of the motion reliability map, the generating of the intermediate view projection image may include increasing a first weight which is assigned to at least one of the intermediate view reprojection images and decreasing a second weight which is assigned to the image that is generated by interpolating the at least two of the original view reprojection images when a determination is made that a distance between the intermediate view reprojection image and the original view reprojection image has decreased.

According to one or more exemplary embodiments, there may be provided an apparatus and method for generating a virtual view in an image reconstruction system that may enhance the accuracy of a motion estimation by three-dimensionally reconstructing an object by using original view projection images photographed in a partial isometric system and by performing reprojection, assuming a full isometric system, and may enhance the quality of an intermediate view which is generated by using a reprojection image.

Further, according to one or more exemplary embodiments, there may be provided a method for generating an intermediate view by using interpolation based on motion between views. Accordingly, the one or more exemplary embodiments may be applicable to other devices, such as, for example, a CT performing a tomosynthesis and a multi-view projection image based reconstruction. In addition, it may be possible to decrease an applied dosage of X-rays.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

Figure 1:
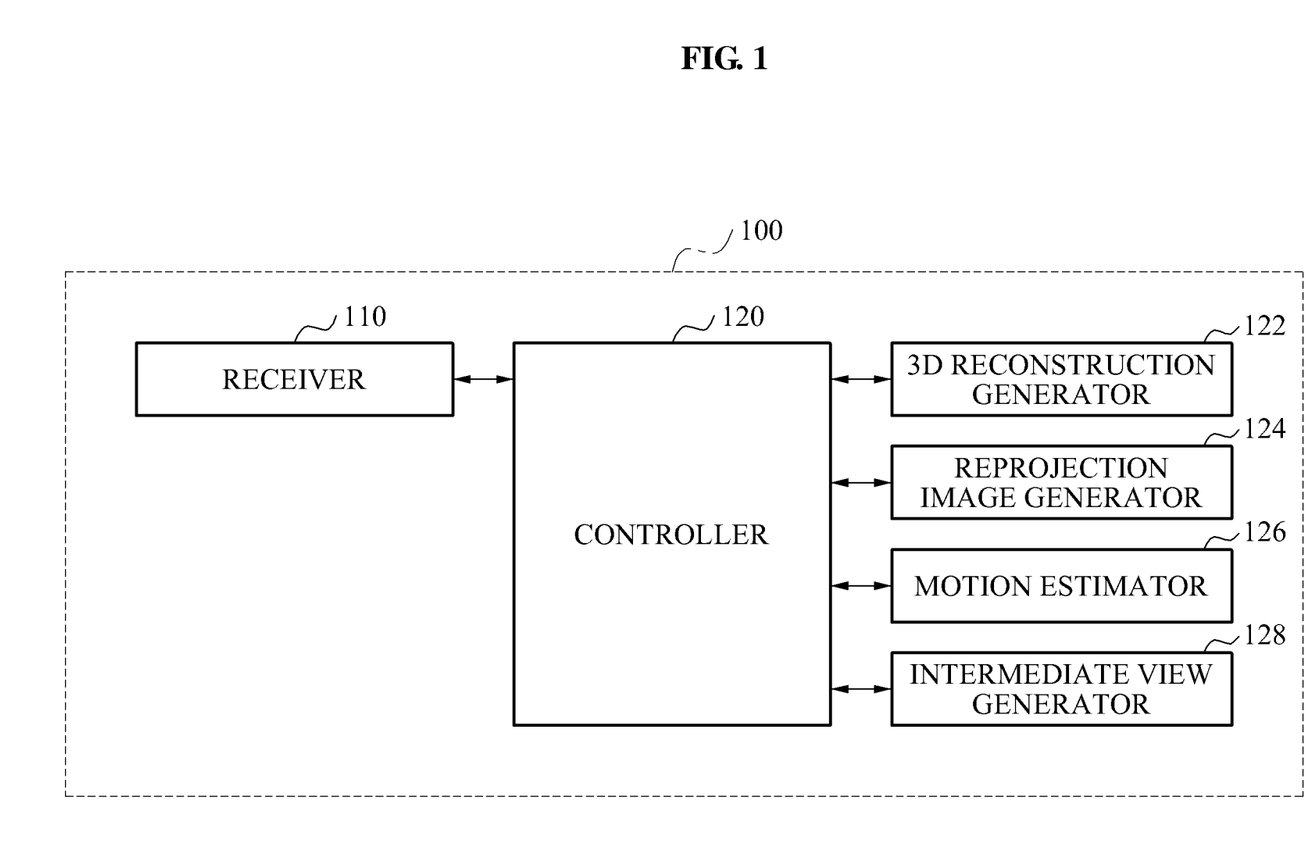
FIG. 1 is a diagram which illustrates an example of a virtual view generating apparatus for generating a virtual intermediate view in an image reconstruction system, according to an exemplary embodiment.

FIG. 1 illustrates an example of a virtual view generating apparatus 100 for generating a virtual intermediate view in an image reconstruction system, according to an exemplary embodiment.

Referring to FIG. 1, the virtual view generating apparatus 100 includes a receiver 110, a controller 120, a three-dimensional (3D) reconstruction generator 122, a reprojection image generator 124, a motion estimator 126, and an intermediate view generator 128.

The receiver 110 may receive original view projection images that are generated by emitting X-rays toward an object via original views. The original view projection images may include data that is generated based on a partial isometric system.

Figure 2:
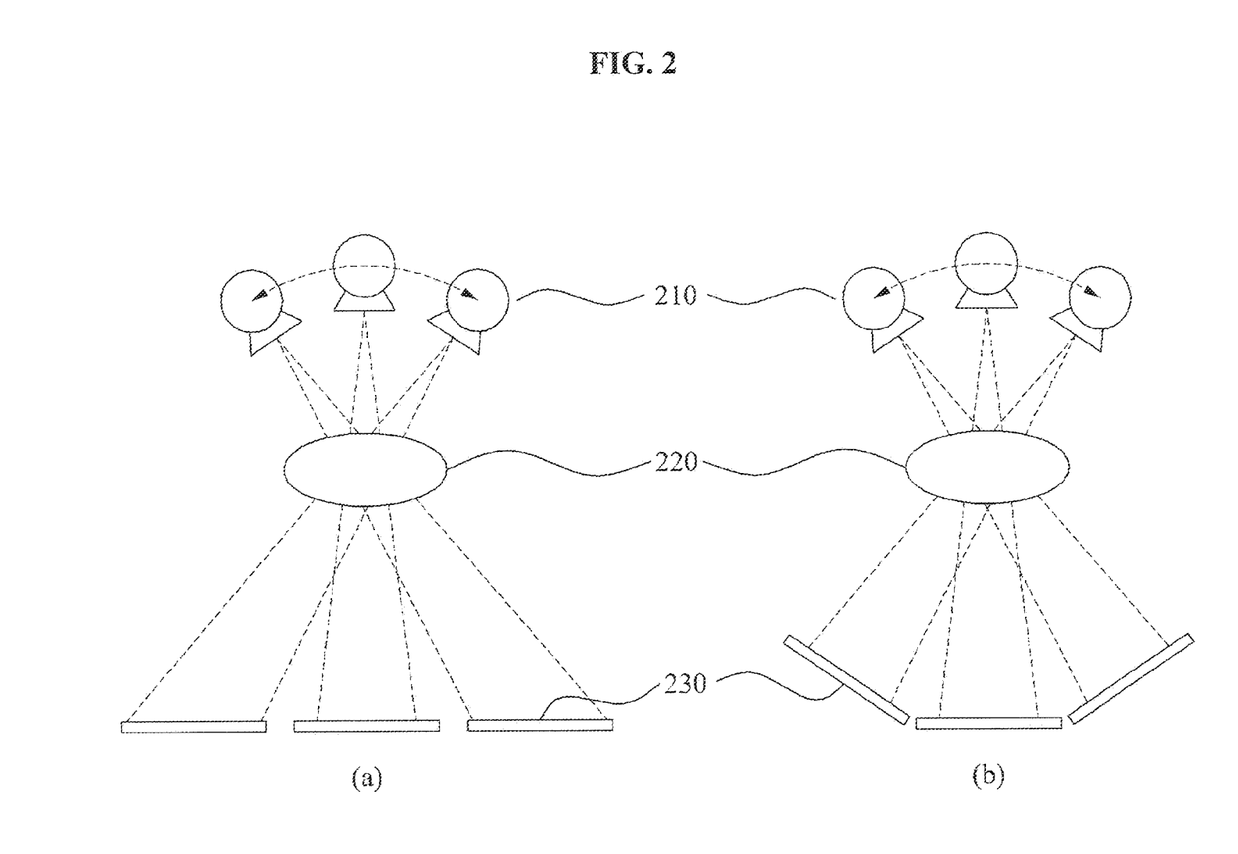
FIG. 2 is a diagram which illustrates an example of a full isometric system and an example of a partial isometric system, according to an exemplary embodiment.

FIG. 2 illustrates an example of a full isometric system and an example of a partial isometric system, according to an exemplary embodiment.

A part (a) of FIG. 2 shows the partial isometric system in which a detector 230 is shifted to one direction when an X-ray emitter 210 rotates to photograph an object 220.

A part (b) of FIG. 2 shows the full isometric system in which the detector 230 also rotates when the X-ray emitter 210 rotates to photograph the object 220.

In general, a tomosynthesis system uses a structure of the partial isometric system, because it is possible to minimize the complexity of a structural portion for moving a detector, and because it is advantageous in a spatial constraint aspect of the system, as compared to the full isometric system in which the detector also rotates. However, in an aspect of generating an intermediate view, the partial isometric system produces a relatively great deformation between neighboring views as compared to the full isometric system and thus, it is difficult to accurately estimate a motion by using a partial isometric system.

The 3D reconstruction generator 122 may generate a 3D object by three-dimensionally reconstructing the object by using the original view projection images.

The 3D reconstruction generator 122 may employ an iterative reconstruction scheme as a reconstruction method. The iterative reconstruction scheme may generate a 3D object to be maximally similar to each original view projection image.

The motion estimator 126 may estimate a motion of the reconstructed 3D object with respect to at least two original view reprojection images by using a block-based motion estimation scheme. Hereinafter, a method for estimating the motion of the reconstructed 3D object will be described with reference to FIG. 3 and FIG. 4.

Figure 3:
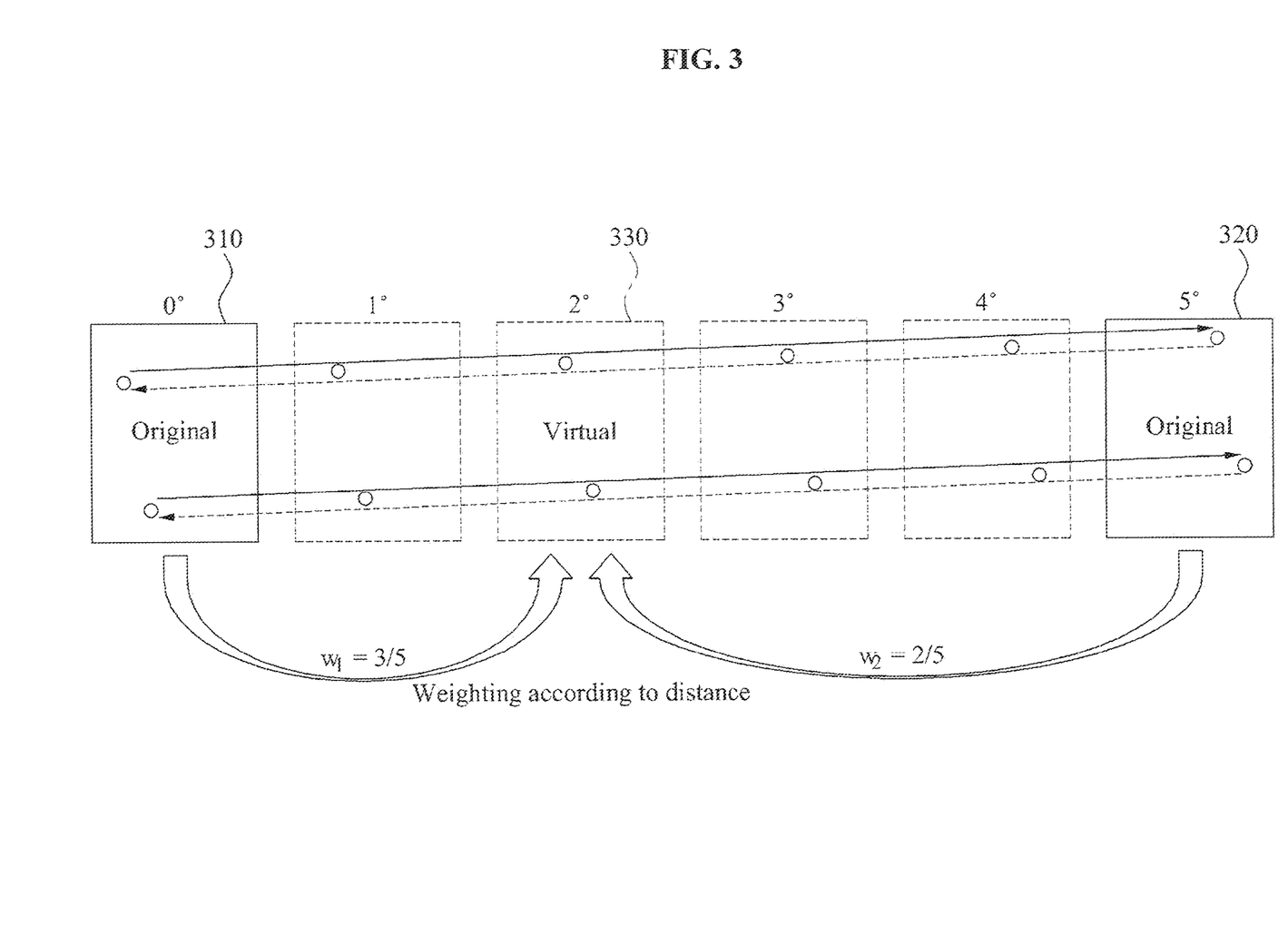
FIG. 3 is a diagram which illustrates an example of a virtual view generating apparatus for generating a virtual intermediate view by using bi-directional motion information, according to an exemplary embodiment.

FIG. 3 illustrates an example of a virtual view generating apparatus for generating a virtual intermediate view by using bi-directional motion information, according to an exemplary embodiment.

Referring to FIG. 3, the motion estimator 126 may operate based on a presumption that a motion of a reconstructed 3D object with respect to original view reprojection images 310 and 320 is bi-directional as indicated by arrow indicators, and may estimate a motion with respect to an intermediate view 330 that occurs with respect to the original view reprojection images 310 and 320.

When estimating the motion with respect to the intermediate view 330, the motion estimator 126 may estimate the motion with respect to the intermediate view by assigning a relatively high contribution value to an original view reprojection image that is closer to the intermediate view 330, based on a position of the intermediate view 330. In particular, the motion estimator 126 may assign a first contribution value to original view reprojection image 310 and a second contribution value to original view reprojection image 320. Further, based on a determination that intermediate view 330 is closer to original view reprojection image 310 than to original view reprojection image 320, in an exemplary embodiment, the assigned first contribution value may be greater than the assigned second contribution value, and a relative magnitude of each of the first and second contribution values may be based on a respective difference between the determined distances between the intermediate view 330 and each of the corresponding original view reprojection images 310 and 320.

Figure 4:
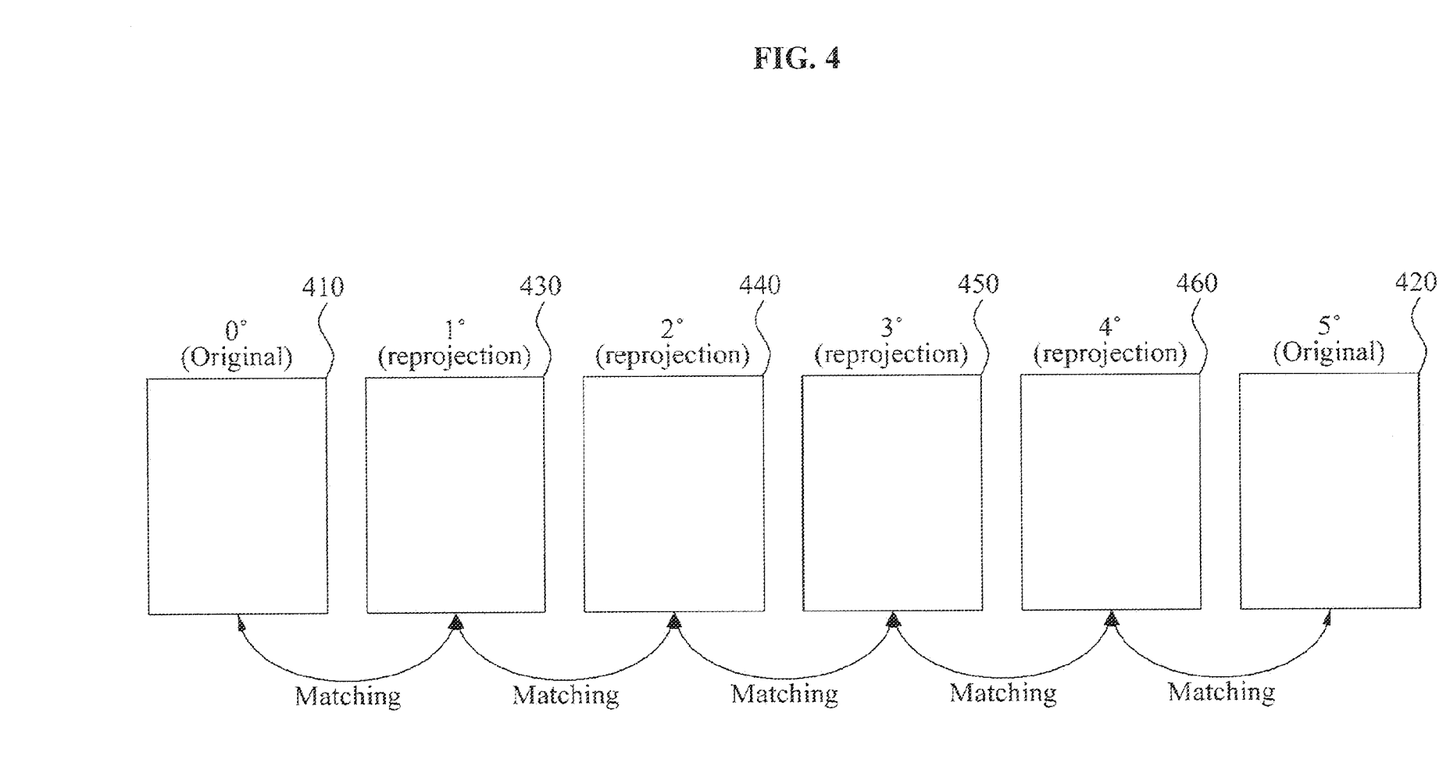
FIG. 4 is a diagram which illustrates an example of a virtual view generating apparatus for estimating a motion by using matching with respect to reprojection images, according to an exemplary embodiment.

FIG. 4 illustrates an example of a virtual view generating apparatus for estimating a motion by using matching with respect to reprojection images, according to an exemplary embodiment.

Referring to FIG. 4, the motion estimator 126 may estimate a motion of a reconstructed 3D object with respect to two adjacent reprojection images from among original view reprojection images 410 and 420 and intermediate view reprojection images 430, 440, 450, and 460, by using the two adjacent reprojection images.

The intermediate view generator 128 may generate an intermediate view projection image with respect to at least two original view reprojection images by using estimated motion information relating to the at least two original view reprojection images.

Prior to generating the intermediate projection image, the intermediate view generator 128 may generate a motion reliability map, and may generate the intermediate view projection image by using the motion reliability map.

Figure 5:
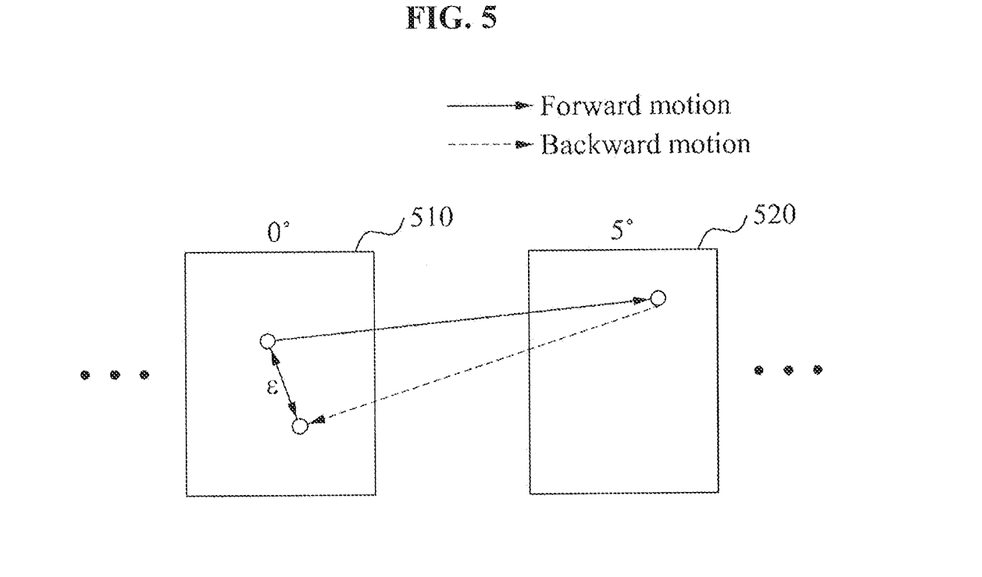
FIG. 5 is a diagram which illustrates an example of determining motion reliability in order to generate a motion reliability map, according to an exemplary embodiment.

The intermediate view generator 128 may generate a motion reliability map as illustrated in FIG. 5 by employing a method which may be executed in accordance with the illustration shown in FIG. 5.

FIG. 5 illustrates an example of determining motion reliability in order to generate a motion reliability map, according to an exemplary embodiment.

Referring to FIG. 5, the intermediate view generator 128 may estimate a motion with respect to original view reprojection images 510 and 520 based on a forward motion estimation and a backward motion estimation, and may generate a motion reliability map by classifying a particular intermediate view and/or a particular area within the motion reliability map as an unreliable area when a difference (shown in FIG. 5 as "$\epsilon$") between a forward estimated motion and a backward estimated motion is greater than a predetermined reference value, and by classifying a particular intermediate view and/or a particular area within the motion reliability map as a reliable area when the difference between the forward estimated motion and the backward estimation motion is less than or equal to the predetermined reference value.

Figure 6:
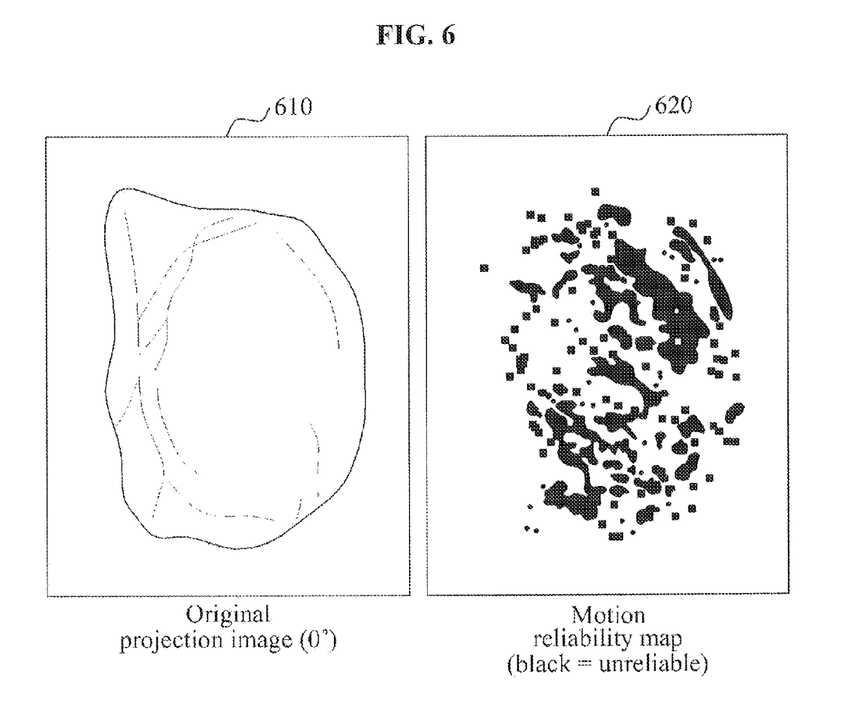
FIG. 6 is a diagram which illustrates an example of a motion reliability map that is generated by a virtual view generating apparatus based on motion reliability, according to an exemplary embodiment.

FIG. 6 illustrates an example of a motion reliability map that is generated by a virtual view generating apparatus based on motion reliability, according to an exemplary embodiment.

Referring to FIG. 6, a left image 610 is an original view projection image of a cross-sectional area of breast tissue, and a right image 620 indicates a motion reliability map of the left image 610. Referring to the motion reliability map, white indicates reliable areas and black indicates unreliable areas.

Hereinafter, a method for generating an intermediate view projection image by using a motion reliability map will be described with reference to FIG. 7 and FIG. 8.

Figure 7:
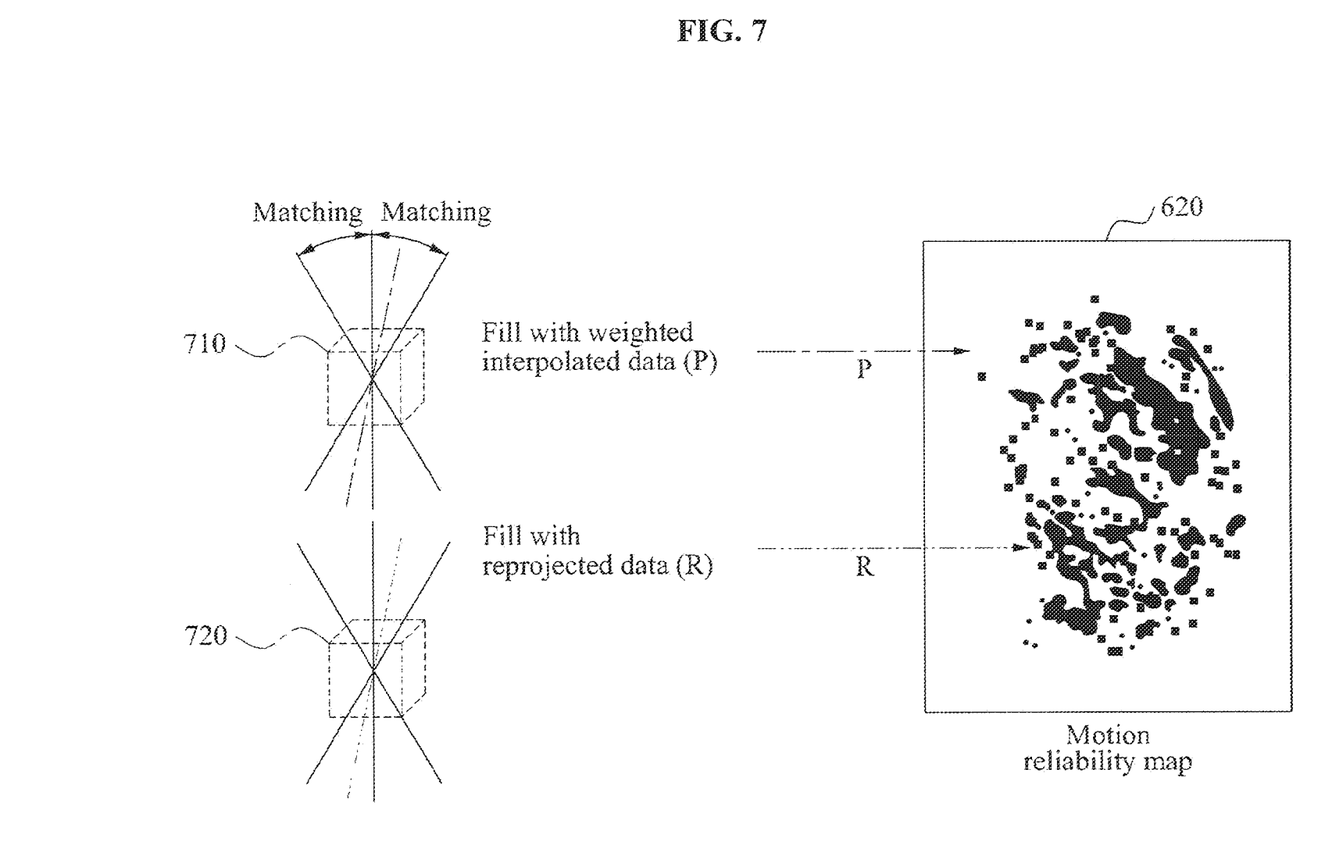
FIG. 7 is a diagram which illustrates an example of using a virtual view generating apparatus for generating a virtual intermediate view by using a motion reliability map, according to an exemplary embodiment.

FIG. 7 illustrates an example of a using a virtual view generating apparatus for generating a virtual intermediate view by using a motion reliability map, according to an exemplary embodiment.

Referring to FIG. 7, the intermediate view generator 128 may generate a motion reliability map 620, and may generate an intermediate view projection by using original view reprojection images in conjunction with a motion interpolation scheme 710 to fill a reliable area of the motion reliability map 620, and by using a region which corresponds to the same position of an intermediate view reprojection image 720 to fill an unreliable area of the motion reliability map 620.

Figure 8:
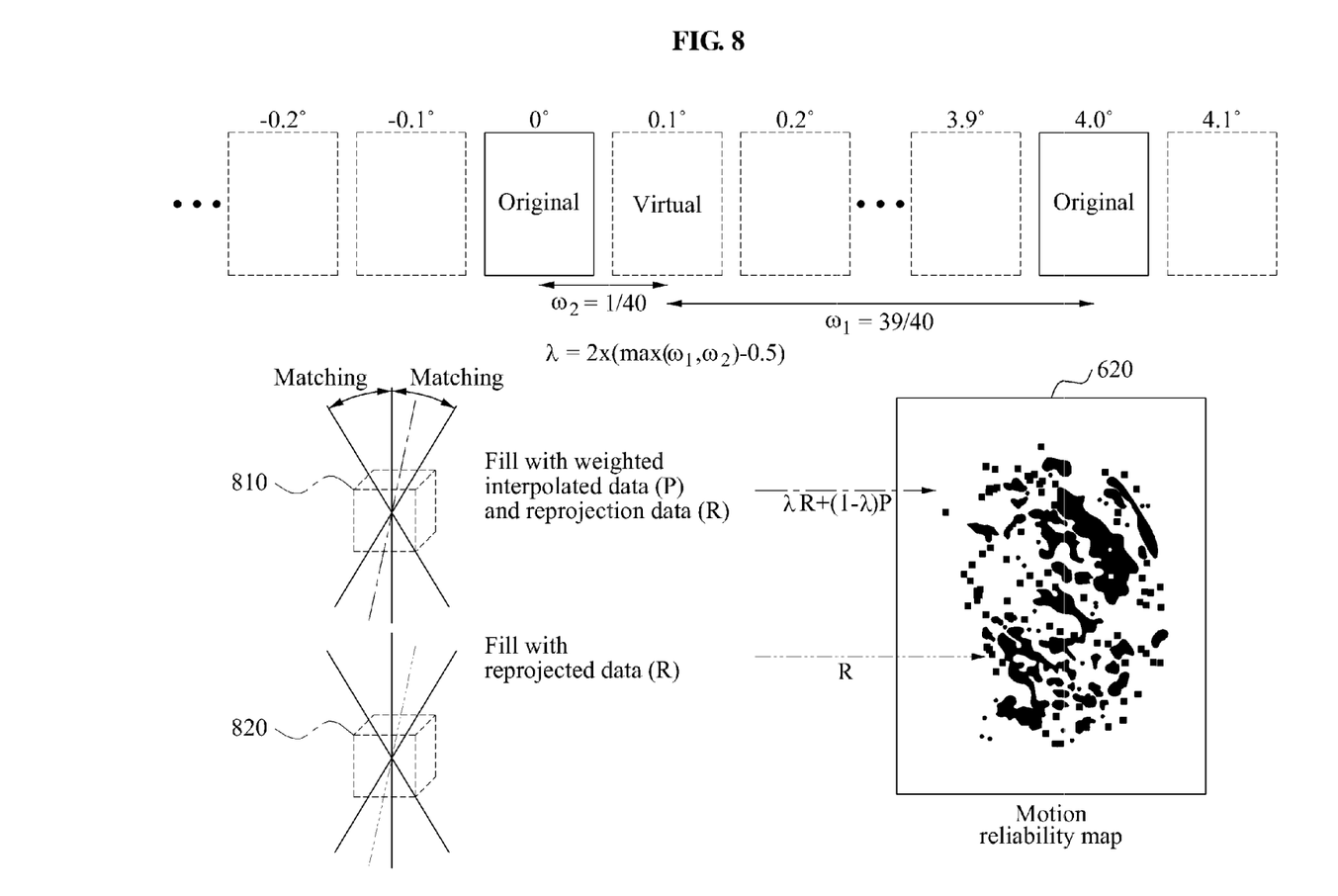
FIG. 8 is a diagram which illustrates another example of using a virtual view generating apparatus for generating a virtual intermediate view by using a motion reliability map, according to an exemplary embodiment.

FIG. 8 illustrates another example of using a virtual view generating apparatus to generate a virtual intermediate view by using a motion reliability map, according to an exemplary embodiment.

The intermediate view generator 128 may generate a motion reliability map 620, and may generate an intermediate view projection image by using an area which corresponds to the same position of an intermediate view reprojection image 820 to fill an unreliable area of the motion reliability map 620, and by using an area which corresponds to the same position of an image 810 that is generated by using a weighted averaging of an image, generated by interpolating original view reprojection images, and the intermediate view reprojection image. In the example illustrated in FIG. 8, a series of 39 intermediate view reprojection images are generated by interpolating, at uniform 0.1° intervals, between a first original view reprojection image labeled as "0°" and a second original view reprojection image labeled as "4°." The interpolation is performed by applying a linear factor $\omega_1 = n/40$ to a respective data point from the first original view reprojection image and a linear factor $\omega_2 = (40-n)/40 = 1-\omega_1$ to a corresponding data point from the second original view reprojection image and then combining all of the derived data points to generate an nth intermediate view reprojection image. The weights are calculated by using the formula $\lambda = 2(\max(\omega_1, \omega_2) - 0.5)$, and the weighted averaging of an image may be generated by weighting the interpolated data P and the reprojection data R according to the formula $\lambda R + \lambda(1-)P$. The motion reliability map 620 is then generated by using a result of the weighted averaging of the image as described above.

The controller 120 may control the overall operation of the virtual view generating apparatus 100. The controller 120 may perform and/or control functions of the 3D reconstruction generator 122, the reprojection image generator 124, the motion estimator 126, and the intermediate view generator 128. The 3D reconstruction generator 122, the reprojection image generator 124, the motion estimator 126, and the intermediate view generator 128 are separately illustrated to describe functions thereof. Accordingly, the controller 120 may include at least one processor which is configured to perform functions of one or more of the 3D reconstruction generator 122, the reprojection image generator 124, the motion estimator 126, and the intermediate view generator 128. Further, the controller 120 may include at least one processor which is configured to perform one or more selected functions of the 3D reconstruction generator 122, the reprojection image generator 124, the motion estimator 126, and the intermediate view generator 128.

Hereinafter, a method for generating a virtual intermediate view by using an image reconstruction system using multiple views according to exemplary embodiments will be described with reference to FIG. 9.

Figure 9:
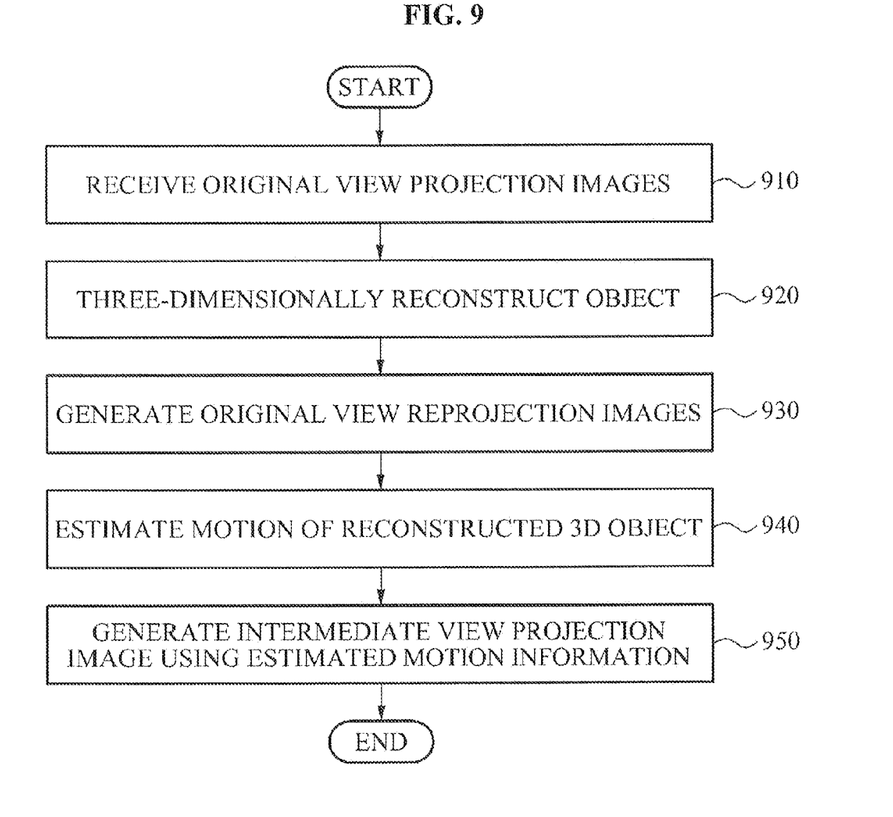
FIG. 9 is a flowchart which illustrates an example of a method for generating a virtual intermediate view by using a virtual view generating apparatus, according to an exemplary embodiment.

FIG. 9 illustrates an example of a method for generating, by using a virtual view generating apparatus 100, a virtual intermediate view.

Referring to FIG. 9, in operation 910, the virtual view generating apparatus 100 receives original view projection images that are generated by emitting X rays toward an object via original views. The original view projection images may include data that is generated based on a partial isometric system.

In operation 920, the virtual view generating apparatus 100 generates a 3D object by three-dimensionally reconstructing the object by using the original view projection images.

In operation 930, the virtual view generating apparatus 100 generates original view reprojection images by virtually emitting X-rays toward the reconstructed 3D object via the original views. In an exemplary embodiment, the generation of the original view reprojection images is based on an assumption of a full isometric system.

In operation 940, the virtual view generating apparatus 100 estimates a motion of the reconstructed 3D object with respect to at least two of the original view reprojection images by using a block-based motion estimation scheme. In particular, the virtual view generating apparatus 100 may perform the estimation based upon an assumption that the motion of the reconstructed 3D object with respect to the original view reprojection images is linear, and may further estimate a motion with respect to an intermediate view that is generated between the original view reprojection images. Alternatively, the virtual view generating apparatus 100 may estimate a motion of the reconstructed 3D object with respect to two adjacent reprojection images from among the original view reprojection images and the intermediate view reprojection images by using the two adjacent reprojection images.

In operation 950, the virtual view generating apparatus 100 generates an intermediate view projection image with respect to the original view reprojection images by using information relating to the estimated motion. The virtual view generating apparatus 100 may generate a motion reliability map, and may generate an intermediate view projection image by using original view reprojection images in conjunction with a motion interpolation scheme to fill a reliable area of the motion reliability map, and by using a region which corresponds to the same position of an intermediate view reprojection image to fill an unreliable area of the motion reliability map. Alternatively, the virtual view generating apparatus 100 may generate a motion reliability map, and may generate an intermediate view projection image by using an area which corresponds to the same position of an intermediate view reprojection image to fill an unreliable area of the motion reliability map, and by using an area which corresponds to the same position of an image that is generated by using weight averaging of an image, generated by interpolating original view reprojection images, and the intermediate view reprojection image to fill a reliable area of the motion reliability map.

According to one or more exemplary embodiments, a method and apparatus for generating a virtual view in an image reconstruction system by using multiple views may enhance the accuracy of motion estimation by three-dimensionally reconstructing an object by using original view projection images that are photographed in a partial isometric system and by performing reprojection based on the assumption of a full isometric system, and may enhance the quality in generating an intermediate view by using a reprojection image with respect to an unreliable area.

Further, according to one or more exemplary embodiments, a method for generating an intermediate view by using interpolation based on motion with respect to views may be applicable, for example, to a tomosynthesis system, and/or to other devices, such as a CT, which are used for performing a multi-view projection image-based reconstruction. Accordingly, by using such a method, it may be possible to decrease an amount of X-rays which might otherwise be emitted with respect to a patient.

In an exemplary embodiment, a program and/or a code for performing the above-described methods may be stored on various types of terminal-readable recording media such as a random access memory (RAM), a flash memory, a read only memory (ROM), an erasable programmable ROM (EPROM), an electronically erasable and programmable ROM (EE-PROM), a register, a hard disk, a removable disk, a memory card, a USB memory, a CD-ROM, an/or any other suitable non-transitory or transitory medium.

A number of exemplary embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for generating a virtual view in an image reconstruction system, the apparatus comprising:
   a receiver which receives original view projection images that are generated by emitting X-rays toward an object via original views;
   a three-dimensional (3D) reconstruction generator which generates a 3D object by three-dimensionally reconstructing the object by using the original view projection images;
   a reprojection image generator which generates original view reprojection images by virtually emitting X-rays toward the reconstructed 3D object via the original views;
   a motion estimator which estimates a motion of the reconstructed 3D object with respect to at least two of the original view reprojection images by using a motion estimation scheme; and
   an intermediate view generator which generates an intermediate view projection image with respect to the at least two of the original view reprojection images by using information relating to the at least two of the original view reprojection images that is estimated by the motion estimator.

2. The apparatus of claim 1, wherein the original view projection images include data that is generated based on a partial isometric system.

3. The apparatus of claim 1, wherein the motion estimator is configured to use a linear motion estimation algorithm for estimating the motion of the reconstructed 3D object with respect to the at least two of the original view reprojection images, and to estimate a motion with respect to the intermediate view projection image that is generated by the intermediate view generator.

4. The apparatus of claim 3, wherein when estimating the motion with respect to the intermediate view projection image, the motion estimator is configured to estimate the motion with respect to the intermediate view projection image by assigning a first contribution value to a first one of the at least two of the original view reprojection images and a second contribution value to a second one of the at least two of the original view reprojection images, wherein when a determination that the first one of the at least two of the original view reprojection images is closer to the intermediate view projection image is made based on the intermediate view projection image, the first contribution value is greater than the second contribution value, and when a determination that the second one of the at least two of the original view reprojection images is closer to the intermediate view projection image is made based on the intermediate view projection image, the second contribution value is greater than the first contribution value.

5. The apparatus of claim 1, wherein:
the reprojection image generator is configured to generate intermediate view reprojection images by virtually emitting X-rays toward the reconstructed 3D object via intermediate views, and
the motion estimator is configured to estimate a motion of the reconstructed 3D object with respect to two adjacent reprojection images from among the original view reprojection images and the generated intermediate view reprojection images by using the two adjacent reprojection images.

6. The apparatus of claim 1, wherein:
the reprojection image generator is configured to generate intermediate view reprojection images by virtually emitting X-rays toward the reconstructed 3D object via intermediate views, and
the intermediate view generator is configured to generate a motion reliability map which corresponds to a first intermediate view that is classified as a reliable area and a second intermediate view that is classified as an unreliable area by using motion information estimated by the motion estimator, and to generate the intermediate view projection image by using the generated original view reprojection images in conjunction with a motion interpolation scheme to fill the reliable area and by using at least one of the generated intermediate view reprojection images to fill the unreliable area.

7. The apparatus of claim 6, wherein the motion estimator is configured to estimate a motion with respect to the at least two of the original view reprojection images based on a forward motion estimation and a backward motion estimation, and the intermediate view generator is further configured to generate the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

8. The apparatus of claim 1, wherein:
the reprojection image generator is configured to generate intermediate view reprojection images by virtually emitting X-rays toward the reconstructed 3D object via intermediate views, and
the intermediate view generator is configured to generate a motion reliability map which corresponds to a first intermediate view that is classified as a reliable area and a second intermediate view that is classified as an unreliable area by using motion information estimated by the motion estimator, and to generate the intermediate view projection image by using the generated intermediate view reprojection images to fill the unreliable area, and by using a weighted averaging of an image that is generated by interpolating the at least two of the original view reprojection images and at least one of the intermediate view reprojection images to fill the reliable area.

9. The apparatus of claim 8, wherein when using the weighted averaging to fill the reliable area of the motion reliability map, the intermediate view generator is further configured to increase a first weight which is assigned to the at least one of the intermediate view reprojection images and to decrease a second weight which is assigned to the image that is generated by interpolating the at least two of the original view reprojection images when a determination is made that a distance between the intermediate view reprojection image and the original view reprojection image has decreased.

10. The apparatus of claim 8, wherein the motion estimator is configured to estimate a motion with respect to the at least two of the original view reprojection images based on a forward motion estimation and a backward motion estimation, and the intermediate view generator is further configured to generate the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

11. A method for generating a virtual view in an image reconstruction system, the method comprising:
receiving original view projection images that are generated by emitting X-rays toward an object via original views;
generating a three-dimensional (3D) object by three-dimensionally reconstructing the object by using the original view projection images;
generating original view reprojection images by virtually emitting X-rays toward the reconstructed 3D object via the original views;
estimating a motion of the reconstructed 3D object with respect to at least two of the original view reprojection images by using a motion estimation scheme; and
generating an intermediate view projection image with respect to the at least two of the original view reprojection images by using motion information.

12. The method of claim 11, wherein the original view projection images include data that is generated based on a partial isometric system.

13. The method of claim 11, wherein the estimating comprises using a linear motion estimation algorithm for estimating the motion of the reconstructed 3D object with respect to the at least two of the original view reprojection images, and estimating a motion with respect to the generated intermediate view projection image.

14. The method of claim 13, wherein when estimating the motion with respect to the generated intermediate view projection image, the estimating comprises estimating the motion with respect to the intermediate view projection image by assigning a first contribution value to a first one of the at least two of the original view reprojection images and a second contribution value to a second one of the at least two of the original view reprojection images, wherein when a determination that the first one of the at least two of the original view reprojection images is closer to the intermediate view projection image is made based on the intermediate view projection image, the first contribution value is greater than the second contribution value, and when a determination that the second one of the at least two of the original view reprojection images is closer to the intermediate view projection image is made based on the intermediate view projection image, the second contribution value is greater than the first contribution value.

15. The method of claim 11, further comprising:
generating intermediate view reprojection images by virtually emitting X-rays toward the reconstructed 3D object via intermediate views,
wherein the estimating comprises estimating a motion of the reconstructed 3D object with respect to two adjacent reprojection images from among the original view reprojection images and the generated intermediate view reprojection images by using the two adjacent reprojection images.

16. The method of claim 11, further comprising:
generating intermediate view reprojection images by virtually emitting X-rays toward the reconstructed 3D object via intermediate views,
wherein the generating of the intermediate view projection image comprises generating a motion reliability map which corresponds to a first intermediate view that is classified as a reliable area and a second intermediate view that is classified as an unreliable area by using estimated motion information, using the generated original view reprojection images in conjunction with a motion interpolation scheme to fill the reliable area and using at least one of the generated intermediate view reprojection images to fill the unreliable area.

17. The method of claim 16, wherein the generating of the intermediate view projection image comprises estimating a motion with respect to the at least two of the original view reprojection images based on a forward motion estimation and a backward motion estimation and generating the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

18. The method of claim 11, further comprising:
generating intermediate view reprojection images by virtually emitting X-rays toward the reconstructed 3D object via intermediate views,
wherein the generating of the intermediate view projection image comprises generating a motion reliability map which corresponds to a first intermediate view that is classified as a reliable area and a second intermediate view that is classified as an unreliable area by using estimated motion information, using the generated intermediate view reprojection images to fill the unreliable area, and using a weighted averaging of an image that is generated by interpolating the at least two of the original view reprojection images and at least one of the intermediate view reprojection images to fill the reliable area.

19. The method of claim 18, wherein when using the weighted averaging to fill the reliable area of the motion reliability map, the generating of the intermediate view projection image comprises increasing a first weight which is assigned to at least one of the intermediate view reprojection images and decreasing a second weight which is assigned to the image that is generated by interpolating the at least two of the original view reprojection images when a determination is made that a distance between the intermediate view reprojection image and the original view reprojection image has decreased.

20. A non-transitory computer readable medium having recorded thereon a program executable by a computer for performing a method for generating a virtual view in an image reconstruction system, the method comprising:
virtually reconstructing a three-dimensional (3D) object by using original view projection images that are generated by emitting X-rays toward an object via original views;
generating original view reprojection images by virtually emitting X-rays toward the virtually reconstructed 3D object via the original views;
using a motion estimation algorithm to estimate a motion of the reconstructed 3D object with respect to at least two of the generated original view reprojection images; and
generating an intermediate view projection image with respect to the at least two of the generated original view reprojection images by using information resulting from the using the motion estimation algorithm.

21. The computer readable medium according to claim 20, wherein the method further comprises generating intermediate view reprojection images by virtually emitting X-rays toward the reconstructed 3D object via intermediate views, and
wherein the generating of the intermediate view projection image comprises generating a motion reliability map which corresponds to a first intermediate view that is classified as a reliable area and a second intermediate view that is classified as an unreliable area by using estimated motion information, using the generated original view reprojection images in conjunction with a motion interpolation algorithm to fill the reliable area, and using at least one of the generated intermediate view reprojection images to fill the unreliable area.

22. The computer readable medium according to claim 21, wherein the generating of the intermediate view projection image comprises estimating a motion with respect to the at least two of the original view reprojection images based on a forward motion estimation and a backward motion estimation and generating the motion reliability map by classifying the second intermediate view as the unreliable area when a difference between a forward estimated motion and a backward estimated motion for the second intermediate view is greater than a predetermined reference value, and by classifying the first intermediate view as the reliable area when the difference between the forward estimated motion and the backward estimation motion for the first intermediate view is less than or equal to the predetermined reference value.

23. The computer readable medium of claim 20, wherein the method further comprises generating intermediate view reprojection images by virtually emitting X-rays toward the reconstructed 3D object via intermediate views, and
wherein the generating of the intermediate view projection image comprises generating a motion reliability map which corresponds to a first intermediate view that is classified as a reliable area and a second intermediate view that is classified as an unreliable area by using estimated motion information, generating the intermediate view projection image by using the generated intermediate view reprojection images to fill the unreliable area, and using a weighted averaging of an image that is generated by interpolating the at least two of the original view reprojection images and at least one of the intermediate view reprojection images to fill the reliable area.

24. The computer readable medium of claim 23, wherein when using the weighted averaging to fill the reliable area of the motion reliability map, the generating of the intermediate view projection image comprises increasing a first weight which is assigned to at least one of the intermediate view reprojection images and decreasing a second weight which is assigned to the image that is generated by interpolating the at least two of the original view reprojection images when a determination is made that a distance between the intermediate view reprojection image and the original view reprojection image has decreased.

* * * * *